(12) United States Patent
Snijder et al.

(10) Patent No.: US 8,408,219 B2
(45) Date of Patent: Apr. 2, 2013

(54) DENTAL TAPE AND PROCESS FOR ITS MANUFACTURING

(75) Inventors: Carina S. Snijder, Sittard (NL);
Christiaan H. P. Dirks, Dilsen (NL);
Leonard J. A. Nielaba, Eygelshoven (NL)

(73) Assignee: DSM IP Assets B.V., Heerlen (NL)

( * ) Notice: Subject to any disclaimer, the term of this patent is extended or adjusted under 35 U.S.C. 154(b) by 678 days.

(21) Appl. No.: 11/794,247
(22) PCT Filed: Dec. 27, 2005
(86) PCT No.: PCT/EP2005/014185
§ 371 (c)(1),
(2), (4) Date: Mar. 17, 2008
(87) PCT Pub. No.: WO2006/074823
PCT Pub. Date: Jul. 20, 2006

(65) Prior Publication Data
US 2008/0156345 A1    Jul. 3, 2008

Related U.S. Application Data
(60) Provisional application No. 60/643,120, filed on Jan. 12, 2005.

(30) Foreign Application Priority Data
Jan. 11, 2005 (EP) ..................................... 05075060

(51) Int. Cl.
| | |
|---|---|
| A61C 15/00 | (2006.01) |
| A45D 7/00 | (2006.01) |
| D02G 3/00 | (2006.01) |
| A61K 8/00 | (2006.01) |
| A61K 8/18 | (2006.01) |
| A61Q 11/00 | (2006.01) |
| B29D 28/00 | (2006.01) |
| D02G 1/20 | (2006.01) |
| D02J 1/22 | (2006.01) |
| B27B 17/00 | (2006.01) |
| D01D 5/12 | (2006.01) |
| B29C 47/88 | (2006.01) |
| A61C 15/04 | (2006.01) |
| B05D 3/00 | (2006.01) |

(52) U.S. Cl. ........ 132/321; 132/200; 428/364; 428/370; 424/49; 264/103; 264/130; 264/210.8; 264/211.14; 264/211.17; 264/290.5; 427/2.29

(58) Field of Classification Search ................... 132/321, 132/323, 325, 329, 200, 324, 328; 433/143; 424/49; 427/2.29; 264/2.5, 103, 130, 210.8, 264/211.14, 211.17, 290.5; 428/364, 370; 57/282, 309
See application file for complete search history.

(56) References Cited

U.S. PATENT DOCUMENTS 3,247,857 A * 4/1966 Kanbar ........................ 132/329
4,545,950 A * 10/1985 Motooka et al. ........... 264/210.6
(Continued)

FOREIGN PATENT DOCUMENTS

| EP | 0 339 935 A | 11/1989 |
|---|---|---|
| EP | 0 662 388 A | 7/1995 |
| EP | 0 740 002 A | 10/1996 |

OTHER PUBLICATIONS

International Search Report mailed May 10, 2006 in PCT/EP2005/014185.

*Primary Examiner* — Todd Manahan
*Assistant Examiner* — Vanitha Elgart
(74) *Attorney, Agent, or Firm* — Nixon & Vanderhye P.C.

(57) ABSTRACT

Dental floss products are provided which include a unitary tape of ultra-high molar mass polyethylene having an intrinsic viscosity of at least 5 dl/g, as measured in decalin at 135° C., the tape having a thickness of about 0.02-0.1 mm and a width of about 0.25-6 mm, and a tensile strength of at least 1.8 GPa. The dental floss products have very high mechanical, especially tensile strength, and show high resistance to tearing and has a low coefficient of friction. The tape can be inserted between teeth tightly together without breaking. A further advantage of the dental tape products is that most of the initial strength during flossing is retained, even if the tape separates into filaments. Processes for making a unitary tape suitable for use in a dental floss product are also provided.

20 Claims, 1 Drawing Sheet

U.S. PATENT DOCUMENTS

| | | | | |
|---|---|---|---|---|
| 4,551,296 A | * | 11/1985 | Kavesh et al. | 264/203 |
| 4,588,633 A | * | 5/1986 | Kono et al. | 428/220 |
| 4,646,766 A | * | 3/1987 | Stallard | 132/325 |
| 4,883,700 A | * | 11/1989 | Harpell et al. | 428/113 |
| 5,113,880 A | * | 5/1992 | Honda et al. | 132/321 |
| 5,407,623 A | * | 4/1995 | Zachariades et al. | 264/119 |
| 5,479,952 A | * | 1/1996 | Zachariades et al. | 132/321 |
| 5,702,657 A | * | 12/1997 | Yoshida et al. | 264/112 |
| 5,741,451 A | * | 4/1998 | Dunbar et al. | 264/103 |
| 6,238,605 B1 | * | 5/2001 | Wimmer | 264/103 |
| 6,951,685 B1 | * | 10/2005 | Weedon et al. | 428/364 |
| 7,025,986 B2 | * | 4/2006 | Brown et al. | 424/443 |
| 7,060,354 B2 | * | 6/2006 | Baillie et al. | 428/364 |
| 7,238,744 B2 | * | 7/2007 | Yaritz et al. | 524/585 |
| 7,344,668 B2 | * | 3/2008 | Tam et al. | 264/210.8 |
| 7,470,459 B1 | * | 12/2008 | Weedon et al. | 428/103 |
| 7,498,369 B2 | * | 3/2009 | Whear et al. | 524/123 |
| 2003/0178044 A1 | * | 9/2003 | Brown et al. | 132/321 |
| 2003/0196676 A1 | * | 10/2003 | Baillie et al. | 132/321 |
| 2006/0243298 A1 | * | 11/2006 | Hamant | 132/321 |

* cited by examiner

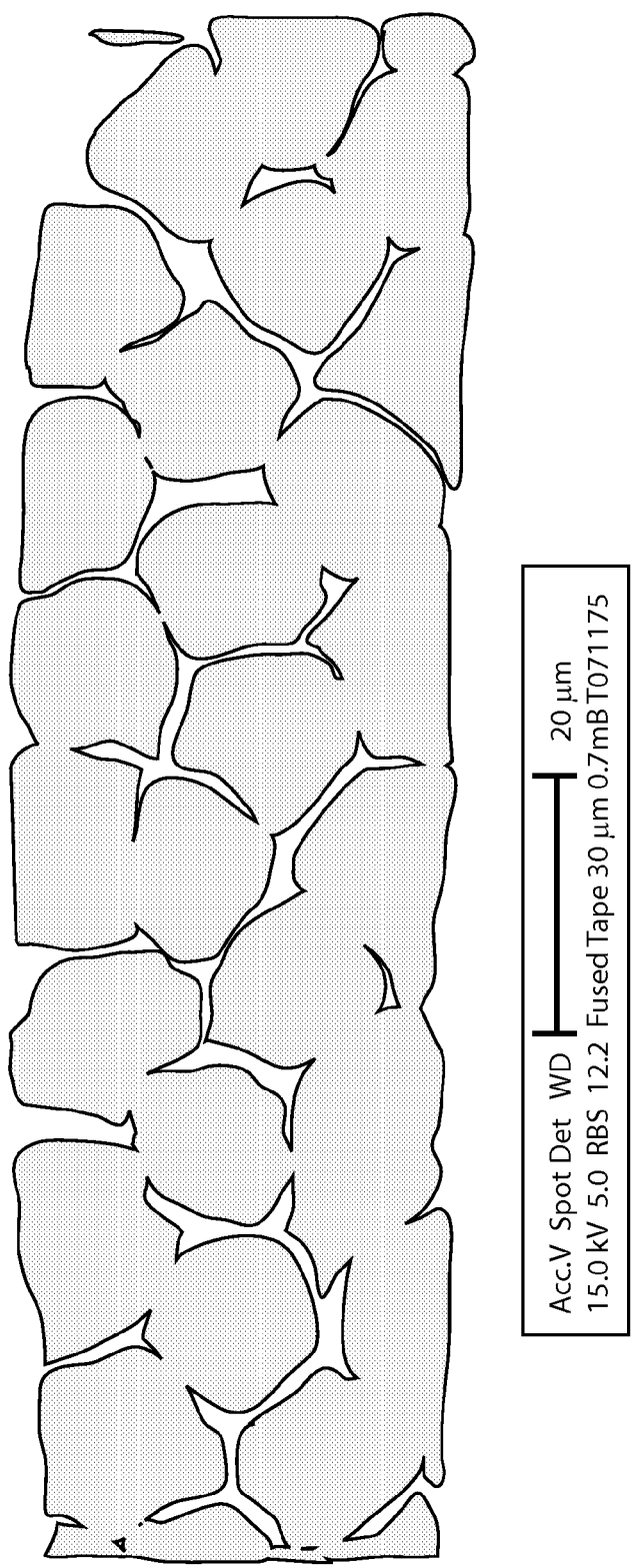

DENTAL TAPE AND PROCESS FOR ITS MANUFACTURING

This application is the US national phase of international application PCT/EP2005/014185 filed 27 Dec. 2005 which designated the U.S. and claims benefit of EP 05075060.3 and US 60/643,120, dated 11 Jan. 2005 and 12 Jan. 2005, respectively, the entire content of which is hereby incorporated by reference.

FIELD

The invention relates to a dental floss product comprising a unitary tape of ultra-high molar mass polyethylene having an intrinsic viscosity of at least 5 dl/g, as measured in decalin at 135° C., the tape having a thickness of about 0.02-0.1 mm and a width of about 0.25-6 mm.

The invention further relates to a process of making a unitary tape suitable for use in a dental floss product.

BACKGROUND AND SUMMARY

A dental floss product is generally advised as a means for treating inter-proximal and sub-gingival areas in the oral cavity to supplement brushing of teeth. Flossing comprises manoeuvring the floss product between teeth, and gently moving up and down against the surface of the teeth to remove inter-dental plaque and debris, including sub-gingival plaque. Plaque is constantly being formed on tooth surfaces, and if not regularly removed plaque can cause tooth cavities and gum disease. During flossing, the floss product should loosen or break up plaque from the surface and transport it away from the teeth. A dental floss product should thus have dimensions that allow insertion and rubbing between teeth, yet be strong enough to withstand the forces accompanied therewith.

The most commonly used dental floss comprises a plurality of filaments, made from polymers like polyamides or polyolefins. Such multi-filament floss is usually waxed to hold the filaments together, and to lubricate the floss. European application EP 0339935 A3 discloses a particular embodiment of a dental floss composed of a multifilament of ultrahigh-molecular weight polyethylene, having good mechanical properties. The dental floss was prepared by bundling a multiplicity of drawn oriented filaments to produce an multifilament having a tensile strength of 2.5 GPa, modulus of 90 GPA and an elongation to break of 4.1%.

An alternative form of dental floss is dental tape, also optionally waxed and flavoured. Both multi-filament and tape floss products are stated to have specific advantages and disadvantages; but selecting the optimum product also appears highly dependent on personal preferences of users.

Such a dental floss product comprising a unitary tape is known from EP 0662388 B1. In this patent specification a dental floss is described that comprises a unitary tape of about 0.03-0.13 mm thickness and of about 0.25-6.4 mm width, which tape is made from ultra-high molar mass polyethylene having a molar mass in the range of 300 to 6000 kg/mol, and which tape has a Young's modulus in the range of 0.5 to 10 GPa and a tensile strength of 0.1 to 1.2 GPa. It is indicated that this tape is not shredding into filaments during use, thereby making flossing more convenient and easier. Another indicated advantage of the product is that it is not coated with a waxy solid, because it is self-lubricating. The tape applied as floss was made by swelling a precursor tape of said polyethylene in paraffin oil into a pseudo-gel state, cooling the pseudo-gel under controlled conditions to ambient temperature, squeezing the swollen tape lightly to remove paraffin oil, treating the tape in hexane and heating the tape to around 70° C. to remove residual hexane to produce a porous tape having a greater porosity than said precursor tape, compressing the porous tape and then stretching the tape at 80-130° C. to obtain a drawn product.

A drawback of the known dental floss tape is that its mechanical properties are not sufficient in all circumstances, especially premature tearing and breakage of the tape may occur for example upon insertion between teeth that have very small inter-dental distance or that virtually contact each other at some point, or during flossing when contacting a sharp edge of for example a brace or bridge.

It is therefore an object of the present invention to provide a dental floss product comprising a unitary tape made from ultra-high molar mass polyethylene that does not, or at least to a reduced extent, show said disadvantage.

This object is achieved according to the invention with a dental floss product wherein the tape has a tensile strength of at least 1.8 GPa.

The dental floss product according to the invention has very high mechanical, especially tensile strength, shows high resistance to tearing and has a low coefficient of friction. The tape can be inserted between teeth tightly together without breaking. A further advantage of the dental tape according to the invention is that it retains most of its initial strength during flossing, even if the tape separates into filaments. Still another advantage is that hardly any pilling of the tape occurs, even upon fibrillation, meaning there is little risk of the tape getting stuck between teeth as a result of local thickening. The dental tape further has a high modulus and shows little elongation during use, allowing a precise and controlled flossing action.

BRIEF DESCRIPTION OF DRAWING

FIG. 1 is an enlarged photographic cross-section of a dental floss tape made in accordance with Example 1 below.

DETAILED DESCRIPTION

The dental floss product according to the invention comprises a unitary tape of ultra-high molar mass polyethylene, which tape is obtainable by a process wherein a ultra-high molar mass polyethylene multi-filament precursor is exposed to a temperature within the melting point range of the polyethylene for a time sufficient to at least partly fuse adjacent filaments while simultaneously stretching the precursor; as is described in more detail later on.

The dental floss product comprises a unitary tape of ultra-high molar mass polyethylene (UHPE). Unitary tape in the present context means that the floss as supplied contains one single tape, in contrast to floss comprising multi-filament yarn.

A unitary tape of UHPE means that UHPE is the major polymeric material from which the tape is made, and which provides the mechanical properties. Preferably, the tape consists for at least 75% (m/m) of UHPE, more preferably at least 80, or at least 85%. The tape may further comprise up to 25% (m/m) of an oil or wax, or a combination thereof, which is compatible or miscible with UHPE above its melting temperature, that is above 150 or above 160° C. Examples of suitable oils and waxes include mineral oils (e.g. heat transfer grade mineral oil with an average molar mass of about 250-700), vegetable oils (e.g. coconut oil), or, preferably nonvolatile, solvents for polyolefin; like paraffin oil or paraffin wax. In a preferred embodiment the tape comprises from about 1 to 20, or 2-16, or 2.5-12% (m/m) of said oil or wax.

Ultra-high molar mass polyethylene has an intrinsic viscosity (IV) of more than 5 dl/g. The IV is determined according to method PTC-179 (Hercules Inc. Rev. Apr. 29, 1982) at 135° C. in decalin, the dissolution time being 16 hours, with DBPC as anti-oxidant in an amount of 2 g/l solution, and the viscosity at different concentrations is extrapolated to zero concentration. Intrinsic viscosity is a measure for molar mass (also called molecular weight) that can more easily be determined than actual molar mass parameters like $M_n$ and $M_w$. There are several empirical relations between IV and $M_w$, for example $M_w=5.37\times10^4 [IV]^{1.37}$ (see EP 0504954 A1), but such relation is dependent on molar mass distribution. The UHPE tape preferably has an IV of between about 6 and 40 dl/g, more preferably between 7 and 35 dl/g, or even between 8 and 30 dl/g. Preferably, the UHPE is a linear polyethylene with less than one branch per 100 carbon atoms, and preferably less than one branch per 300 carbon atoms, a branch or side chain containing at least 10 carbon atoms. The linear polyethylene may further contain up to 5 mol % of one or more co-monomers, such as alkenes like propylene, butene, pentene, 4-methylpentene or octene.

The UHPE can be a single polymer grade, but also a mixture of two or more different polyethylene grades, e.g. differing in IV or molar mass distribution, and/or type and number of co-monomers or side chains. The UHPE tape in the floss product according to the invention may further contain small amounts, generally less than 5% (m/m), preferably less than 3% (m/m) of customary additives, such as anti-oxidants, thermal stabilizers, colorants, flow promoters, etc.

The dental floss product according to the invention comprises a unitary tape of ultra-high molar mass polyethylene having a thickness of about 0.02-0.1 mm and a width of about 0.25-6 mm. The thickness of the tape is related to average distances between teeth; which may vary widely between persons. The thickness is preferably about 0.03-0.09 or 0.04-0.08 mm to provide a balance between easy insertion, convenient handling and strength. The width of the tape may also vary considerably, but is preferably about 0.3-5, 0.4-4, or even 0.5-3 mm to balance easy manoeuvring and effective plaque removal. The width to thickness or aspect ratio of the dental tape is not critical and may vary widely. Expressed in textile units, the tape typically has a linear density or titre of about 50-5000 dtex, preferably about 100-3000, or 150-2500 dtex. A tape of lower titre is generally more flexible and easier in use.

The dental floss product according to the invention comprises a unitary tape of ultra-high molar mass polyethylene having a tensile strength of at least 1.8 GPa. Although a tape of such strength will not easily break as a result of a user applying too high a force, it is found that a higher strength is beneficial for preventing rupture during passing between teeth with tight contacts. Preferably, the tape has thus a tensile strength, also simply referred to as strength, of at least 2.0, 2.2, 2.4 or 2.6 GPa. Maximum strength of the tape is limited for practical reasons, such as availability of suitable yarn as precursor, see later, and is about 5 GPa. Tensile strength, also simply strength, or tenacity are determined by known methods, as based on ASTM D885-85 or D2256-97.

In one embodiment of the dental floss product according to the invention the UHPE tape is non-fibrillating during use. Some users find such dental tape more convenient and more effective for flossing. A non-fibrillating tape can for example have been obtained by a process, wherein a precursor multi-filament UHPE yarn is thermally fused, while carefully controlling temperature and exposure time to promote fusion, and optionally applying a pressure during fusing.

In another embodiment of the dental floss product according to the invention the UHPE tape shows fibrillation during use, that is the tape separates into clusters of one or more filaments. The advantage of such fibrillating tape is that during flossing the tape spreads out into filaments or clusters of filaments, which provide a more effective cleaning action on the surface of a tooth. An advantage of the tape according to the invention is that the filaments formed are rather flexible and soft, and show little risk of damaging the gum. Such fibrillating tape can for example have been obtained by a process wherein a precursor multi-filament UHPE yarn is thermally fused, while carefully controlling the degree of fusion via adjusting conditions like temperature and exposure time, to result in a unitary tape that is incipiently fibrillatable.

It is true that an incipiently fibrillatable tape for use as dental floss is described in U.S. Pat. No. 4,646,766, but this publication does not disclose or suggest to make high-strength tapes made from UHPE, let alone by a process of thermally fusing multi-filament yarn.

In a preferred embodiment, the UHPE tape is fibrillatable during use, but retains at least 75% of its initial strength after fibrillation. The tape according to the invention does not break as a result of shredding, but fibrillates into filaments or clusters thereof, which are of high strength as well. Preferably, the fibrillated or at least partially fibrillated tape still has strength at least 80, or even 90% of its initial strength. An advantage of such tape is that there are no or very little broken filaments. Normally broken filaments tend to curl up to form locally thicker parts, often called pilling. A dental floss showing pilling may get stuck between teeth; which presents a higher risk of damaging the gum or even teeth when the user applies a high force in reaction.

In a preferred embodiment, the dental floss product according to the invention comprises a unitary tape of ultra-high molar mass polyethylene, which tape has a surface that is not completely smooth, but has a certain surface structure or roughness. Such textured tape can for example result from making a UHPE tape by a process comprising thermally fusing multi-filament yarn, optionally twisted, whereby the original filament structure is still partially retained, or some filaments have not fused together at the surface of the tape. Such tape shows protrusions and/or grooves on its surface, together hereinafter simply called grooves, which are typically predominantly oriented in the lengthwise direction, preferably of a size in the range of 0.002-0.05 mm, depending on the dimensions of the tape itself. The advantages of such a dental tape include that it slides easily between and over teeth, yet its small surface grooves help breaking up and removing plaque, resulting in more effective cleaning.

Preferably, the grooves are of a size, that is width and depth or height, of at least about 0.003, 0.004, or even 0.005 mm; to effect a more effective breaking up of plaque. The dimension, especially the depth, of a groove is preferably at most about 0.04 mm, or at most 0.03 mm; to result in a tape with good strength. In case of a tape that has been made by thermally fusing a plurality of filaments, the groove dimensions typically are similar to or smaller than the dimension of a filament.

The grooves on the tape surface are predominantly oriented along the length of the tape, but may also be at an angle with the length direction, preferably at an angle of about 0-45°, more preferably about 0-30°, or even 0-20°. A tape with such surface grooves is found to more effectively remove loosened particles/plaque from between teeth.

The dental floss product according to the invention may further comprise the usual waxes and other additives. The tape can for example by coloured, preferably with a colorant that is non-saliva soluble, but that is soluble in an apolar agent, like a mineral oil or paraffin wax. The dental floss product may also contain various coatings such as a wax (other than the oil or wax mentioned before), or other, preferably saliva-soluble additives. Customary additives include fluoride-containing compounds, flavourings, fragrances, small abrasive particles, or medicinal materials, for example to attack bacteria in plaque.

The invention further relates to a process of making a unitary tape suitable for use in a dental floss product from a UHPE precursor material.

Such a process for making a unitary tape is known from EP 0662388 B1. In this patent specification a dental floss is described that comprises a unitary tape that was made by a process comprising swelling a precursor tape of UHPE in paraffin oil into a pseudo-gel state, cooling the pseudo-gel under controlled conditions to ambient temperature, squeezing the swollen tape lightly to remove paraffin oil, treating the tape in hexane and heating the tape to around 70° C. to remove residual hexane to produce a porous tape having a greater porosity than said precursor tape, compressing the porous tape and then stretching the tape at 80-130° C. to obtain a drawn product.

A disadvantage of this known process is that it results in a tape that is prone to rupture upon inserting between teeth with tight contacts.

The object of the present invention is to provide a process that enables making a unitary tape having a thickness of about 0.02-0.1 mm and a width of about 0.25-6 mm, made from a ultra-high molar mass polyethylene precursor, which tape does not show said disadvantage.

This object is achieved according to the invention with a process wherein the precursor is a multi-filament strand, and the process comprises exposing the precursor to a temperature within the melting point range of the polyethylene for a time sufficient to at least partly fuse adjacent filaments while simultaneously stretching the precursor.

With the process according to the invention a tape of specific dimensions can be made that shows a high tensile strength. A further advantage is that the tendency to fibrillate and the surface roughness of the tape can be controlled via the fusion conditions, such as exposure time and temperature.

A process wherein UHPE filaments are at least partially fused together at elevated temperature is known from EP 0740002 B1, but in this publication making of monofilament fishing lines is described, not making of tapes of the present dimensions.

A multi-filament strand is understood to be an article of indefinite length comprising a plurality of filaments made from UHPE. A precursor can be of various constructions, it is for example a braided or laid cord or rope, or a plied, folded or twisted yarn, or an air-entangled yarn. Use of a multi-filament yarn, optionally twisted, has the advantage that the precursor and tape can be made easily and cost-effectively. Preferably, at least 80% (m/m) of the filaments in the multi-filament strand are UHPE filaments, more preferably at least 90% (m/m), and most preferably the strand essentially consists of UHPE filaments; to result in a tape of high strength and low abrasion resistance.

UHPE filaments and multi-filament yarn, can be prepared by spinning of a solution of UHPE in a suitable solvent into a gel fibre and drawing the fibre before, during and/or after partial or complete removal of the solvent; that is via a so-called gel-spinning process. Gel spinning of a solution of UHPE is well known to the skilled person; and is described in numerous publications, including EP 0205960 A, EP 0213208 A1, U.S. Pat. No. 4,413,110, GB 2042414 A, EP 0200547 B1, EP 0472114 B1, WO 01/73173 A1, and in Advanced Fiber Spinning Technology, Ed. T. Nakajima, Woodhead Publ. Ltd (1994), ISBN 1-855-73182-7, and in references cited therein.

The process according to the invention comprises the step of exposing the precursor to a temperature within the melting point range of the UHPE for a time sufficient to at least partly fuse adjacent filaments. The conditions of this fusion step are chosen such, that the temperature and time of exposure are sufficient to soften especially a surface layer of the filaments and to allow them to fuse at least partly to form a unitary tape. The melting point range of the UHPE is the temperature range between the peak melting point of a non-oriented polymer and the peak melting point of a constrained highly-oriented UHPE fibre, as determined by DSC analysis using a scan-rate of 20° C./min. For UHPE filaments, typically showing a melting point range of 138-162° C., the exposing temperature is preferably within the range from about 150° C. up to about 157° C. Residence times during which the precursor is exposed to the fusion temperature may vary within a broad range, but are typically within the range from about 5 seconds to about 1500 seconds. Although higher temperatures tend to enhance the fusion process, care should be taken not to apply too high a temperature or too long a time as this may cause loss in strength of the product, resulting from e.g. partial melting or other molecular relaxation effects within the core of the filaments. Suitable means for performing this process include ovens with accurate temperature control and drawing means; which are known to the skilled person, as well as alternative means for performing the process according to the invention.

During the fusion process, the appearance of the precursor may typically change from an initial, opaque appearance, for example of white colour, into a translucent, milky, or even substantially transparent appearance of the tape, depending on the degree of fusion, type of precursor material, and optional additives. The light transmission of the product generally increases with increased degree of fusion between filaments.

A high degree of fusion, resulting in a translucent tape wherein virtually all filaments are fused together to form a product with a smooth surface, is preferred for making a dental tape product that shows little or no tendency to fibrillate during use. The degree of fusion can be adjusted by varying exposure temperature and time in the process according to the invention. The degree of fusion can be additionally promoted by applying a force to one or both surfaces of the tape during the process; for example by compressing the precursor by guiding it between a pair of rollers, or by pulling it over a member, such as a freely rotating or driven roller, or over a bar. This member is preferably also temperature controlled, more preferably at a temperature setting of 1 or 2 degrees higher than the oven air; especially in case of making a non-fibrillating tape. This results in a smoother surface appearance, and improves abrasion resistance of the monofilament-like product. The pressure exerted on the precursor (or tape) can be adjusted by changing the tension in the line and/or by changing the length of the contacting surface between precursor line and the member (for example by adjusting the diameter of a cylindrical roller or bar). The skilled person can find desirable combinations by some experimentation.

For making a smooth tape, the surface of above member is also flat and smooth. If a specific surface texture for the tape is desired, the member is preferably provided with a surface texture.

The degree of fusion can be determined on the product obtained, for example by visual evaluation, e.g. with the naked eye or by using an optical or electron microscope, of the surface and/or a cross-section. Another possibility is to determine the amount and rate of absorption of a coloured liquid, e.g. from a marker, as described in EP 0740002 B1. The degree of fusion can also be derived from a simple test, wherein the product is repeatedly abraded over a surface, e.g. a metal rod and the number of movements is determined after which the unitary tape product disintegrates into its constituting filaments.

The process according to the invention includes simultaneously stretching the precursor. Stretching means that a draw ratio, also called stretch ratio, of greater than 1.0 is applied to the precursor, in this way keeping the filaments under tension and preventing that the strength of the filaments decreases as a result of thermal molecular relaxation processes. Preferably, a draw ratio of at least 1.5, 2.0 or even at least 2.5 is applied to further improve properties, especially tensile strength of the resulting tape. Above a certain draw ratio this effect levels off, or properties may even decrease as result of partly damaging or breaking of filaments. In addition, the higher the draw ratio, the lower the titre of the resulting product. The maximum draw ratio is thus dependent on the type of precursor and its filaments, and is generally at most about 10, or at most 8 or 6.

The dimensions of the tape to be obtained can be controlled by factors such as the titre of the precursor strand, the number and thickness of its filaments (filament titre, typically expressed in denier per filament or dpf); the twist or entanglement level of yarn; the degree of spreading of the filaments before fusion; and the degree of stretching during fusion.

In a preferred embodiment the process according to the invention further comprises spreading of the filaments of the precursor before fusing. The degree of filament spreading is a way to control tape thickness and width. Spreading of e.g. a multifilament yarn can be done by known methods, for example by guiding the yarn over so-called spreading bars. A minimum tape thickness corresponds largely to at least two layers of filaments contacting each other; otherwise fusion will not be effective. Preferably, the precursor contains at least 3 layers of filaments after spreading for better fusion and control of the degree of fusion. For the same reason, the precursor preferably contains at least one multi-filament yarn having a slight twist, more specifically a yarn with a twist level defined by a twist factor (also called twist multiplier) of from 0 to 0.5; more preferably of 0.01-0.4. Such twist level helps controlling the number of filament layers after spreading, and promotes fusion because filaments are better contacted, thus enabling making of thin unitary tapes. Such twist level also results in at least part of the filaments being oriented at an angle with the length direction of the tape. A higher twist level generally leads to a thicker tape, and to a larger angle of orientation.

The degree of spreading, and thus width of the tape, can be further limited and controlled by providing grooves or protuberances on the spreading bar, and/or subsequent guiding rollers and bars in the process; the distance between protuberances or the width of a groove defining the maximum attainable tape width. The surfaces between the protuberances or inside a groove and all other guiding members affect the form of the tape, and are preferably flat.

The precursor that is used in the process according to the invention can contain UHPE filaments with a filament diameter or titre that varies widely. In general, thicker filaments are applied in a process that includes a relatively high draw ratio, of e.g. greater than 2 or 2.5. Suitable filament thickness is in the range of 0.2 to 15 dpf; preferably the precursor contains filaments with thickness of about 0.3-12, or 0.5-10 dpf, to result in a tape of high strength.

During the process according to the invention, the filaments are drawn and fused together, and a tape of certain strength is made. Preferably, the strength of the tape is at least 1.8 GPa. Preferably, the precursor has an initial strength of at least 1.0 GPa, more preferably of at least 1.5, 1.8, or even 2.0 GPa. The higher the strength of the precursor, the less stretching during the fusion process is needed to make a high strength tape.

The process according to the invention further comprises cooling of the tape after fusing and stretching of filaments. Preferably, the tape obtained with the process according to the invention is cooled while keeping it under tension. This has the advantage that the orientation in the product obtained upon fusing and stretching, on both level of filaments and on molecular level, is retained better. Such tension can result from, for example, winding the tape product into packages subsequent to preceding steps of the process, and cooling the package.

The process according to the invention can further comprise a preceding step of pre-treating the precursor, or one or more of the yarns therein, in order to enhance inter filament bonding during the fusion step. Such pre-treatment step may include coating the precursor with a component or a composition; scouring the precursor, that is washing-off surface components like spin finishes etc.; or applying a high-voltage plasma or corona treatment, or any combination thereof. Preferably, the precursor contains filaments that are substantially free from spin finish, meaning no spin finish was applied in their production, or a spin finish present is substantially removed in a pre-treating step. This has the advantage that fusion effectiveness is improved, and that abrasion resistance of the tape product is further increased.

In another preferred embodiment the precursor is pretreated by applying an effective amount of an oil or wax, e.g. by dipping or wetting; for example a mineral oil, a vegetable oil, or a, preferably non-volatile, solvent for polyolefin; like paraffin oil or wax. This pre-treatment step may be performed at ambient conditions, or at elevated temperature up to below the melting temperature range of the polyolefin fibre, and may even coincide with stretching and fusing. The advantage of this embodiment is that the efficiency of the fusing process is further enhanced, that is a higher degree of fusion at the same conditions, or a similar degree at slightly lower temperature, shorter time or less pressure can be attained.

In a special embodiment the oil or solvent may further comprise other additives, like colorants, fragrances or flavourings. Such additives should of course be stable enough to withstand the subsequent fusing and stretching process. The advantage of this embodiment is that a coloured or flavoured tape can be obtained in a 1-step process. These additives can be oil-soluble or saliva-soluble, depending on whether leaching of the additive into the oral cavity during flossing is desired.

The process according to the invention can further comprise a step wherein a coating composition is applied to the tape after fusing and drawing to form a coating layer. Such coating composition may comprise another wax and other usual additives for dental floss, preferably saliva-soluble additives.

A dental floss product can be any known product comprising the dental tape and suitable for flossing. Typical examples include a hand-held container or dispenser comprising a length of tape, from which a desired length can be dispensed;

or a hand-held device with two protruding parts between which a piece of tape is provided.

The invention further relates to a method for treating interproximal and sub-gingival areas in the oral cavity comprising flossing said areas with a dental floss product according to the invention.

The invention will now be further illustrated with the following experiments.

EXAMPLE 1

As precursor (feed) material a non-twisted gel-spun UHPE yarn was applied, which yarn comprised 100 filaments, had a yarn titre of 243 dtex, a tensile strength of 35.1 cN/dtex, a tensile modulus of 1242 cN/dtex, and an elongation at break of 3.3%.

The precursor was passed through a bath of liquid paraffin as pre-treatment step, and excess oil was wiped off by passing between non-woven fabrics. The paraffin content was calculated to be about 11 mass % by determining the mass increase upon this step. The precursor was guided over a first set of driven rollers, and then over a spreading bar into an oven, kept at a constant temperature of 153.6° C., with a constant speed of 4.0 m/min. Inside the oven the precursor was guided over some cylindrical bars with smooth surface, to reach a length a 8.4 m in the oven. At the exit of the oven, the line was guided over a second set of driven rollers. The speed of the second rollers was 7.2 m/min, resulting in a draw ratio of 1.8, and the draw rate in the oven was about 0.4 $min^{-1}$.

The tape obtained was somewhat translucent, and showed integrity during rubbing between fingers.

The tensile strength (or strength), the tensile modulus (also modulus) and elongation at break (eab) are defined and determined on multifilament yarns, and on tapes as specified in ASTM D885M with a Zwick 1435 tester, using a nominal gauge length of the fibre of 500 mm, a crosshead speed of 50%/min and Instron 2714 clamps. For calculation of the strength, the tensile forces measured are divided by the titre, as determined by weighing 10 meters (or another length) of fibre. Elongation is the measured elongation at break, expressed in % of the original length after clamping the specimen.

The obtained tape has a titre of 146 dtex; a tensile strength of 36.7 cN/dtex, a modulus of 1447 cN/dtex, and elongation at break of 3.2%.

The tape has a width of about 0.5 mm and a thickness of about 30 micron. Under an optical microscope small grooves were visible, mainly in the length direction and especially on one of the surfaces.

The tape was further examined by electron microscopy. First, paraffin oil was extracted from the tape with n-hexane for a few minutes. After drying the tape was embedded in an epoxy resin. Cross-sections of the tape were prepared with a cryo-microtome using a diamond knife. After sectioning the block face samples were fixed into a sample holder and coated with a conductive carbon layer. For imaging a Philips CP SEM XL30 was used with an acceleration voltage of 15 kV in combination with a Robinson backscatter detector. In FIG. 1 part of a cross-section is shown, wherein the darker areas are the filaments and the brighter parts the embedding resin. It can be seen that on one side all filaments appear to have been fused together, and the surface appears rather smooth. On the other side there are some clear openings between filaments, which are visible as predominantly length-wise grooves on the surface. The areas filled with resin indicate that the filaments were partly fused.

Tendency of the tape to fibrillate was determined by moving about 25 cm length of tape to and fro over a metal bar of 3 mm diameter, with a frequency of about 1 Hz and a tension equalling about 4% of the tensile strength of the tape, at ambient temperature and in dry state. After 15 cycles several filaments had separated from the tape; only few of which were broken. After 35 cycles the number of filaments had increased, but there was still a tape. The experiment was stopped after 100 cycles, when the tape was fully fibrillated.

EXAMPLE 2

In the same way as in Ex. 1 a tape was made from the indicated precursor yarn, but now the yarn had been twisted with a twist factor 0.2. Tensile properties were virtually the same; but the tape showed a higher degree of fusion; as also apparent from a lower tendency to fibrillate: first filaments appeared only after 30 cycles, and after 100 cycles the tape was not yet fully fibrillated.

The invention claimed is:

1. A dental floss product comprising a unitary tape of ultra-high molar mass polyethylene having an intrinsic viscosity of at least 5 dl/g, as measured in decalin at 135° C., the tape having a thickness of about 0.02-0.1 mm and a width of about 0.25-6 mm, wherein the tape has a tensile strength of at least 1.8 GPa, and wherein the unitary tape consists of a multi-filament yarn with adjacent filaments of the yarn being at least partially melt-fused one to another.

2. The dental floss product according to claim 1, wherein the polyethylene is linear and has an intrinsic viscosity of between 7 and 35 dl/g.

3. The dental floss product according to claim 1, wherein the tape has a tensile strength of at least 2.0 GPa.

4. The dental floss product according to claim 1, wherein the tape is non-fibrillating during use.

5. The dental floss product according to claim 1, wherein the tape shows fibrillation during use.

6. The dental floss product according to claim 5, wherein the tape retains at least 75% of its initial strength after fibrillation.

7. The dental floss product according to claim 1, wherein the tape shows grooves on its surface.

8. A process of making a unitary dental floss tape, having a thickness of about 0.02-0.1 mm, a width of about 0.25-6 mm and a predetermined degree of fibrillation during use, which process comprises;
    exposing an ultra-high molar mass polyethylene multi-filament strand precursor to a temperature within the melting point range of the polyethylene for a time sufficient to at least partly fuse adjacent filaments while simultaneously stretching the precursor, and
    varying the temperature and time of exposure of the ultra-high molar mass polyethylene multi-filament strand precursor to achieve a desired degree of fusion between adjacent filaments thereof and thereby in turn controllably obtain a predetermined degree of fibrillation of the unitary tape during use.

9. The process according to claim 8, wherein the temperature is within the range from about 150° C. up to about 157° C.

10. The process according to claim 8, wherein the precursor contains at least one twisted multi-filament yarn with a twist factor of 0.01-0.4.

11. The process according to claim 8, wherein the precursor contains filaments that are substantially free from spin finish.

12. The process according to claim 8, further comprising pre-treating the precursor by applying an oil or wax.

13. The process according to claim 12, wherein the oil or wax comprises an additive.

14. A dental floss product comprising a unitary tape of ultra-high molar mass polyethylene having an intrinsic viscosity of at least 5 dl/g, as measured in decalin at 135° C., the tape having a thickness of about 0.02-0.1 mm, a width of about 0.25-6 mm and a predetermined degree of fibrillation during use, wherein the tape has a tensile strength of at least 1.8 GPa, wherein the tape is obtained by a process comprising:

exposing a ultra-high molar mass polyethylene multi-filament strand precursor to a temperature within the melting point range of the polyethylene for a time sufficient to at least partly fuse adjacent filaments while simultaneously stretching the precursor, and varying the temperature and time of exposure of the ultra-high molar mass polyethylene multi-filament strand precursor to achieve a desired degree of fusion between adjacent filaments thereof and thereby in turn controllably obtain a predetermined degree of fibrillation of the unitary tape during use.

15. The dental floss product according to claim 14, wherein the polyethylene is linear and has an intrinsic viscosity of between 7 and 35 dl/g.

16. The dental floss product according to claim 14, wherein the tape has a tensile strength of at least 2.0 GPa.

17. The dental floss product according to claim 14, wherein the tape is non-fibrillating during use.

18. The dental floss product according to claim 14, wherein the tape shows fibrillation during use.

19. The dental floss product according to claim 18, wherein the tape retains at least 75% of its initial strength after fibrillation.

20. The dental floss product according to claim 14, wherein the tape shows grooves on its surface.

* * * * *